US011123525B2

(12) United States Patent
Hanamura et al.

(10) Patent No.: US 11,123,525 B2
(45) Date of Patent: Sep. 21, 2021

(54) WIRE FOR MEDICAL DEVICE AND MEDICAL DEVICE

(71) Applicant: OLYMPUS CORPORATION, Hachioji (JP)

(72) Inventors: Naoyasu Hanamura, Tokyo (JP); Hiroaki Kasai, Tokyo (JP); Hisamitsu Kuwabara, Tokyo (JP); Kohei Shiramizu, Kawasaki (JP); Takuya Fujihara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 406 days.

(21) Appl. No.: 16/203,183

(22) Filed: Nov. 28, 2018

(65) Prior Publication Data
US 2019/0091449 A1    Mar. 28, 2019

Related U.S. Application Data

(63) Continuation of application No. PCT/JP2017/023954, filed on Jun. 29, 2017.

(30) Foreign Application Priority Data

Jul. 12, 2016   (JP) .............................. JP2016-137448

(51) Int. Cl.
*A61M 25/09*       (2006.01)
*A61B 17/122*     (2006.01)
(Continued)

(52) U.S. Cl.
CPC ........... *A61M 25/09* (2013.01); *A61B 1/0014* (2013.01); *A61B 17/12022* (2013.01);
(Continued)

(58) Field of Classification Search
CPC ........ A61M 25/09; A61M 2025/09108; A61M 2025/09133; A61M 2025/09191; A61B 2017/00853; A61B 5/6851
See application file for complete search history.

(56) References Cited

U.S. PATENT DOCUMENTS

| 6,520,214 B1 * | 2/2003 | Sugiyama .......... A61B 1/00071 138/119 |
| 2002/0010386 A1 * | 1/2002 | Matsushita ........... A61L 29/085 600/140 |

(Continued)

FOREIGN PATENT DOCUMENTS

| JP | 2000166858 A | 6/2000 |
| JP | 2009254761 A | 11/2009 |

(Continued)

OTHER PUBLICATIONS

International Search Report (ISR) dated Sep. 5, 2017 issued in International Application No. PCT/JP2017/023954.
(Continued)

*Primary Examiner* — Sean P Dougherty
(74) *Attorney, Agent, or Firm* — Holtz, Holtz & Volek PC

(57) ABSTRACT

A wire for a medical device includes a wire body and a solid lubrication film. The wire body has an outer circumferential layer formed of a plurality of metal strands that are twisted with each other. The solid lubrication film is formed at least on outside exposed surfaces of the plurality of metal strands. When a virtual circle as a smallest circle enclosing the outer circumferential layer is assumed in a cross section perpendicular to a central axis of the wire body, a part of an outer edge of the solid lubrication film of the cross section is inside the virtual circle and a cross-sectional area of the solid lubrication film in the cross section satisfies A/B>0.7 where
(Continued)

A is a size of a portion outside the virtual circle and B is a size of a portion inside the virtual circle.

15 Claims, 10 Drawing Sheets

(51) Int. Cl.
| | |
|---|---|
| *A61B 17/128* | (2006.01) |
| *A61B 1/00* | (2006.01) |
| *A61B 17/12* | (2006.01) |
| *A61M 25/00* | (2006.01) |
| *A61B 17/00* | (2006.01) |
| *A61B 5/00* | (2006.01) |

(52) U.S. Cl.
CPC ...... *A61B 17/1227* (2013.01); *A61B 17/1285* (2013.01); *A61M 25/0054* (2013.01); *A61B 1/00071* (2013.01); *A61B 5/6851* (2013.01); *A61B 2017/00845* (2013.01); *A61B 2017/00853* (2013.01); *A61M 2025/09108* (2013.01); *A61M 2025/09125* (2013.01); *A61M 2025/09133* (2013.01); *A61M 2025/09191* (2013.01)

(56) References Cited

U.S. PATENT DOCUMENTS

| | | | | |
|---|---|---|---|---|
| 2004/0082879 | A1* | 4/2004 | Klint | A61F 2/95 600/585 |
| 2008/0004546 | A1* | 1/2008 | Kato | A61M 25/09 600/585 |
| 2008/0281230 | A1* | 11/2008 | Kinoshita | A61M 25/09 600/585 |
| 2011/0319872 | A1* | 12/2011 | Kawasaki | A61M 25/09 604/528 |
| 2012/0059279 | A1* | 3/2012 | Kawasaki | A61L 31/022 600/585 |
| 2013/0110001 | A1* | 5/2013 | Miyata | A61M 25/09 600/585 |
| 2015/0088036 | A1* | 3/2015 | Takada | A61M 25/09 600/585 |

FOREIGN PATENT DOCUMENTS

| | | |
|---|---|---|
| JP | 2010207321 A | 9/2010 |
| JP | 2012157378 A | 8/2012 |

OTHER PUBLICATIONS

Written Opinion dated Sep. 5, 2017 issued in International Application No. PCT/JP2017/023954.

* cited by examiner

US 11,123,525 B2

WIRE FOR MEDICAL DEVICE AND MEDICAL DEVICE

The application is a continuation application based on a PCT Patent Application No. PCT/JP2017/23954, filed Jun. 29, 2017, whose priority is claimed on Japanese Patent Application No. 2016-137448, filed Jul. 12, 2016. The content of both the PCT Application and the Japanese Applications are incorporated herein by reference.

FIELD OF THE INVENTION

The present invention relates to a wire for a medical device and a medical device.

DESCRIPTION OF RELATED ART

A stranded wire is sometimes used in a medical device. For example, in the medical device such as a medical endoscope, an endoscopic device or the like, the stranded wire is adopted for a manipulation wire, a guide wire, or the like.

The stranded wire used in the medical device is frequently inserted into a tubular member such as, for example, a coil sheath, an endoscopic channel, a catheter, or the like, and moved forward/backward in the tubular member.

In the stranded wire inserted into the tubular member, there is a need to reduce sliding friction against an inner circumferential surface of the tubular member for a light and smooth operation. For example, it is disclosed in Japanese Unexamined Patent Application, First Publication No. 2009-254761 that a manipulation wire that is advanced/retracted in a coil pipe at a treatment tool for an endoscope is sometimes coated with a synthetic resin film having lubricity.

SUMMARY OF THE INVENTION

A wire for a medical device of a first aspect of the present invention includes: a wire body having an outer circumferential layer formed of a plurality of metal strands that are twisted with each other; and a solid lubrication film formed at least on outside exposure surfaces of the plurality of metal strands. In a section of at least a part of the wire body in a longitudinal direction, when a virtual circle as a smallest circle enclosing the outer circumferential layer is assumed in a cross section perpendicular to a central axis of the wire body, a part of an outer edge of the solid lubrication film of the cross section is inside the virtual circle, and a cross-sectional area of the solid lubrication film in the cross section satisfies A/B>0.7 where A is the size of a portion outside the virtual circle and B is the size of a portion inside the virtual circle.

According to a wire for a medical device of a second aspect of the present invention, in the first aspect, a thickness of the solid lubrication film may be 0.01 mm or less at a portion where the outer edge of the cross section is inside the virtual circle.

According to a wire for a medical device of a third aspect of the present invention, in the first aspect, the solid lubrication film may contain solid particles of a fluorine resin.

According to a wire for a medical device of a fourth aspect of the present invention, in the first aspect, the fluorine resin may be polytetrafluoroethylene (PTFE).

A medical device of a sixth aspect of the present invention includes a wire for a medical device that has a wire body having an outer circumferential layer formed of a plurality of metal strands that are twisted with each other; and a solid lubrication film formed at least on outside exposure surfaces of the plurality of metal strands that constitute the outer circumferential layer. In a section of at least a part of the wire body in a longitudinal direction, when a virtual circle as a smallest circle enclosing the outer circumferential layer is assumed in a cross section perpendicular to a central axis of the wire body, a part of an outer edge of the solid lubrication film of the cross section is inside the virtual circle, and a cross-sectional area of the solid lubrication film in the cross section satisfies A/B>0.7 where A is the size of a portion outside the virtual circle and B is the size of a portion inside the virtual circle.

DETAILED DESCRIPTION OF THE INVENTION

Hereinafter, a medical device and a wire for the medical device of an embodiment of the present invention will be described with reference to the attached drawings.

Figure 1:
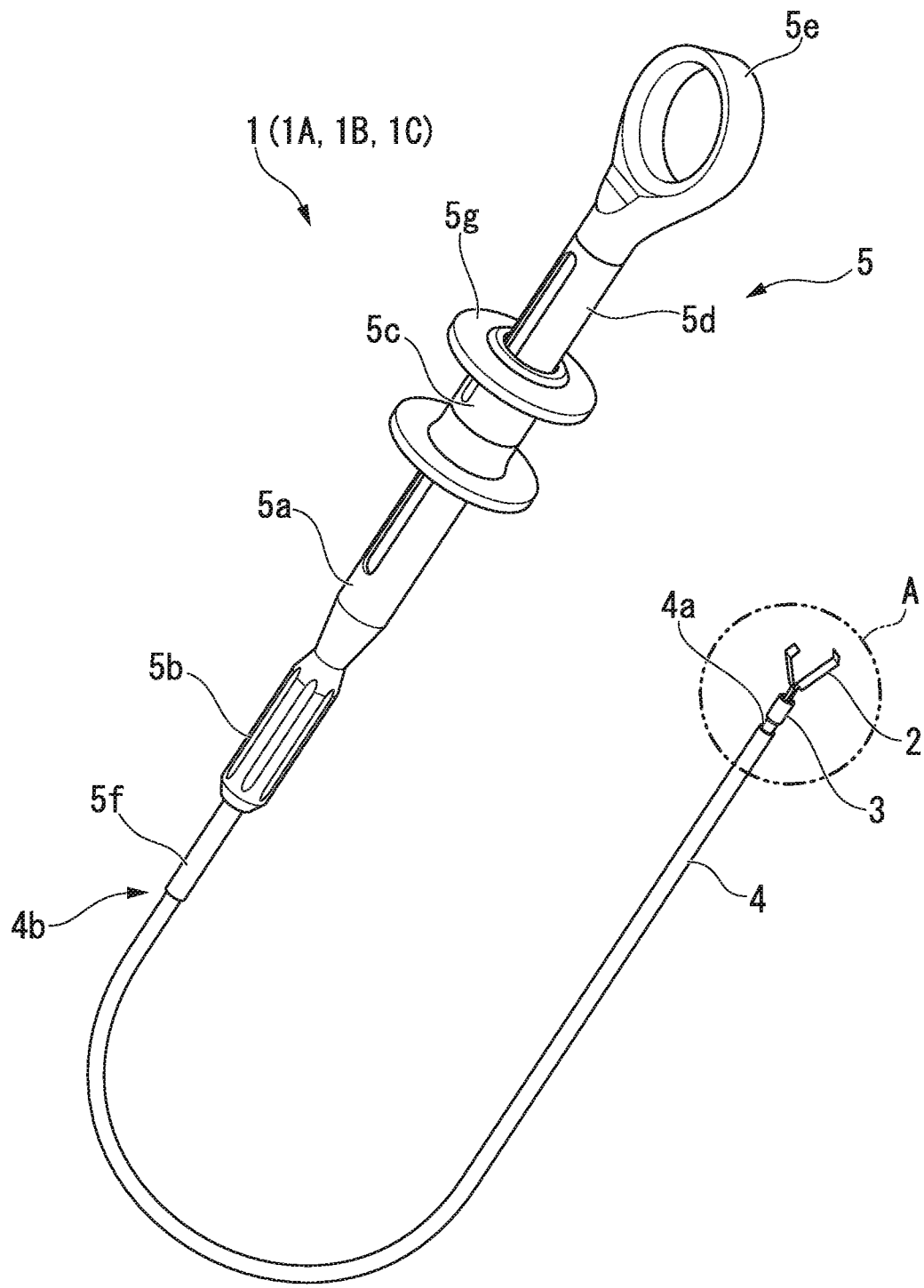
FIG. 1 is a schematic perspective view showing a constituent example of a medical device of an embodiment of the present invention.
Figure 2:
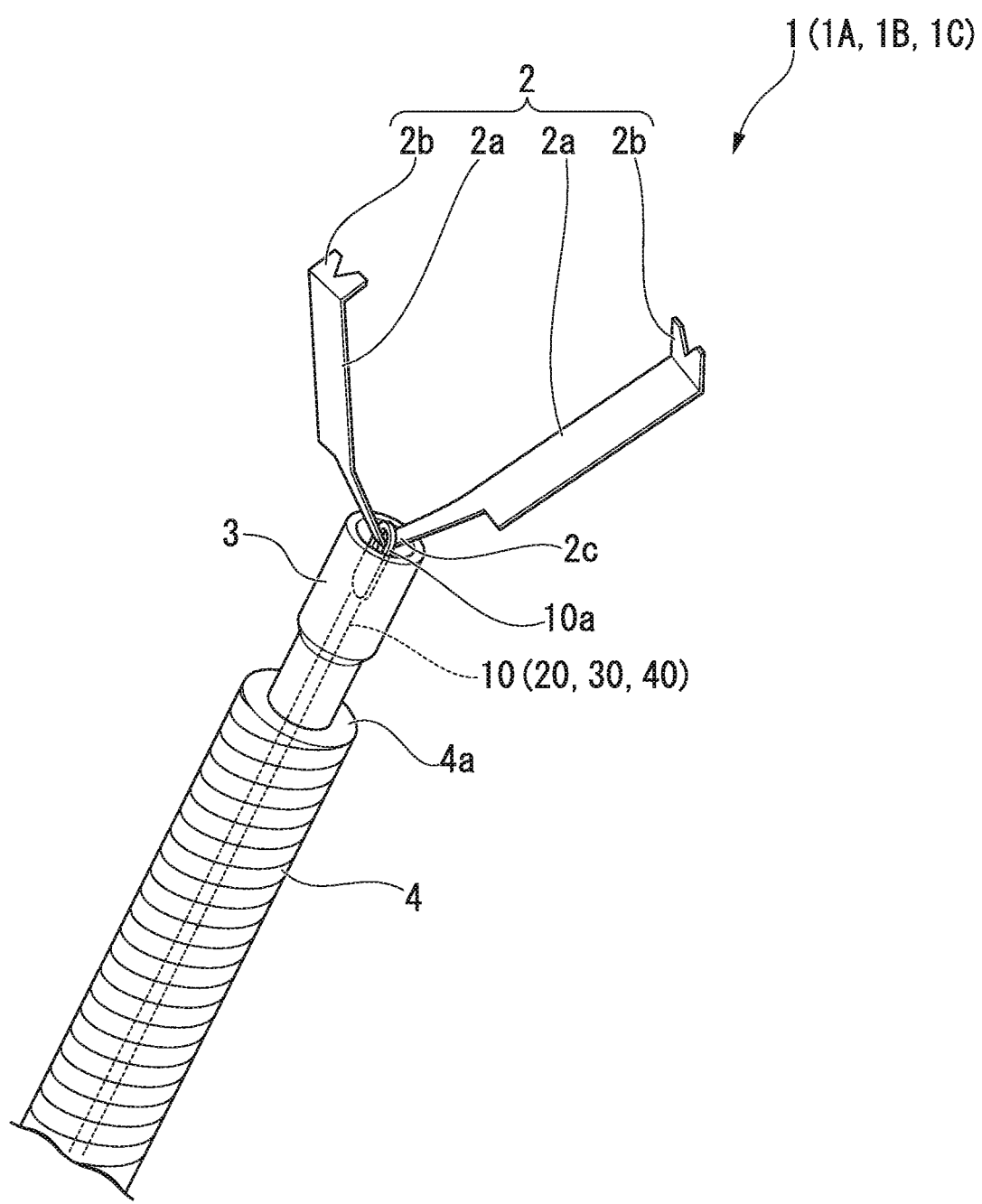
FIG. 2 is an enlarged view of a part A in FIG. 1.

FIG. 1 is a schematic perspective view showing a constituent example of a medical device of the embodiment of the present invention. FIG. 2 is an enlarged view of a part A in FIG. 1.

In each figure, a shape and dimensions for the schematic view are exaggerated (which is also equally true of the following figures).

An endoscopic device (a medical device) 1 of the present embodiment shown in FIG. 1 is a rotary clip device that inserts and places a clip 2 into and in a body cavity of a living body. When used, the endoscopic device 1 can be inserted into the body cavity of the living body, for example, by going through an endoscopic channel or the like.

The endoscopic device 1 includes the clip 2, a pushing tube 3, a manipulation wire (a wire for medical equipment) 10, a coil sheath 4, and a manipulator 5.

The clip 2 is a device that can perform hemostasis or the like in tissue, for example, by gripping the tissue.

As shown in FIG. 2, the clip 2 includes strip-like gripping portions 2a that are bent at a bent portion 2c in a V shape, and gripping claws 2b that protrude from tips of the gripping portions 2a in directions opposite to each other.

The clip 2 is formed of a metal strip-like member having biocompatibility and an appropriate spring property.

The pushing tube 3 is a tubular member for changing an opening width of the clip 2 by inserting the clip 2 from the bent portion 2c and elastically deforming the gripping portions 2a. Furthermore, the pushing tube 3 can lock the clip 2 in a state in which an end close to the bent portion 2c of the clip 2 that grips a gripping target is drawn in.

An opening in which the clip 2 can rotate about a central axis of the pushing tube 3 in a state in which the bent portion 2c of the clip 2 is drawn inside is formed in a distal portion of the pushing tube 3.

An inner diameter of the pushing tube 3 is a size in which the clip 2 folded at the bent portion 2c can be inserted and the clip 2 drawn inside can be locked in the pushing tube 3 by an elastic restoring force of the gripping portions 2a.

The pushing tube 3 is formed of a metal having biocompatibility.

The manipulation wire 10 is a member that transmits a driving force for advancing/retracting the clip 2 with respect to the pushing tube 3 in order to change an amount of insertion of the clip 2 into the pushing tube 3. Furthermore, the manipulation wire 10 is a member that transmits a driving force for rotating the clip 2 in a state in which the bent portion 2c of the clip 2 is drawn into the pushing tube 3 to some extent.

An end of the manipulation wire 10 is provided with, for example, an engaging portion 10a that is formed in a ring shape and is engaged with the bent portion 2c of the clip 2. The engaging portion 10a is configured to be removed from the bent portion 2c when a tensile force above a certain level is applied in a direction away from the clip 2.

The engaging portion 10a may be formed as a part of the manipulation wire 10, or may be formed of a member independent of the manipulation wire 10 and be joined to the end of the manipulation wire 10.

A detailed constitution of the manipulation wire 10 will be described below.

The coil sheath 4 is a tubular member that slidably inserts the manipulation wire 10. The coil sheath 4 has an inner diameter that is slightly larger than an outer diameter of the manipulation wire 10.

The coil sheath 4 is formed by closely winding metal in a coil shape. The coil sheath 4 can be bent without substantially expanding/contracting in a longitudinal direction.

The pushing tube 3 is detachably fitted into a first end 4a of the coil sheath 4 from the outside of the coil sheath 4 toward the inside of the coil sheath 4.

As shown in FIG. 1, a second end 4b of the coil sheath 4 which is located opposite to the first end 4a is coupled with a distal portion 5f of the manipulator 5 to be described below.

Hereinafter, in a longitudinal direction of the endoscopic device 1, an end close to the first end 4a of the coil sheath 4 is referred to as a distal end, and an end close to the manipulator 5 is referred to as a proximal end. A direction directed from the proximal end to the distal end is an inserting direction of the endoscopic device 1.

As shown in FIG. 1, the manipulator 5 includes the distal portion 5f, a holder 5a, a slide shaft 5d, and a slider 5c.

The distal portion 5f is a tubular member to which the second end 4b of the coil sheath 4 is fixed. The manipulation wire 10 inserted into the coil sheath 4 is inserted into the distal portion 5f to be able to be advanced/retracted and to be rotatable about a central axis of the manipulation wire 10.

The holder 5a is a tubular member that is fitted around an outer circumferential portion of the distal portion 5f and is provided to be rotatable about an axis of the distal portion 5f. A rotary grip 5b having a concave-convex portion for rotatably manipulating the holder 5a is formed on an outer circumferential portion of an end of the holder 5a which is close to the distal portion 5f.

The slide shaft 5d is a shaft-like member that is fixed to a proximal portion (not shown) of the distal portion 5f on an inner side of the holder 5a. The slide shaft 5d is disposed on the same axis as a central axis of the holder 5a. The slide shaft 5d is inserted into a central portion of the holder 5a, and extends beyond a proximal end of the holder 5a. A ring portion 5e on which an operator places the operator's finger is formed at a proximal end of the slide shaft 5d.

The slider 5c is a tubular member that is fitted around the slide shaft 5d and is advanced/retracted inside and outside the holder 5a in a direction in which the slide shaft 5d extends.

The slider 5c is engaged with the holder 5a. Since the slider 5c is engaged with the holder 5a, the slider 5c can be rotated about a central axis of the slide shaft 5d integrally with the holder 5a, and be advanced/retracted along the central axis of the slide shaft 5d.

A proximal portion of the slider 5c is provided with a flange 5g on which an operator places the operator's fingers. The flange 5g protrudes outward from the proximal portion of the slider 5c in a radial direction.

An end of the manipulation wire 10 which extends from the distal portion 5f is fixed to a distal portion (not shown) of the slider 5c which is inside the holder 5a.

With this constitution, an operator supports the manipulator 5 with one hand, for example, in a state in which the operator's finger is placed on the ring portion 5e, and manipulates the flange 5g with the other fingers or the other hand, so that the operator can move the slider 5c in an axial direction of the slide shaft 5d. In this way, the operator can perform manipulation for advancing/retracting the manipulation wire 10 coupled to the slider 5c and the slider 5c in the axial direction of the slide shaft 5d.

The operator can support the manipulator 5 with one hand, for example, in a state in which the operator's finger is placed on the ring portion 5e, and rotate the rotary grip 5b with the other hand about an axial direction of the distal portion 5f (rotational manipulation). When the rotary grip 5b is rotated, the holder 5a and the slider 5c coupled to the holder 5a rotate about an axis of the distal portion 5f. In this case, since a rotational driving force is transmitted to the proximal portion of the manipulation wire 10 coupled to the slider 5c, the manipulation wire 10 rotates about the central axis thereof.

Next, a detailed constitution of the manipulation wire 10 that is the wire for a medical device of the present embodiment will be described.

Figure 3:
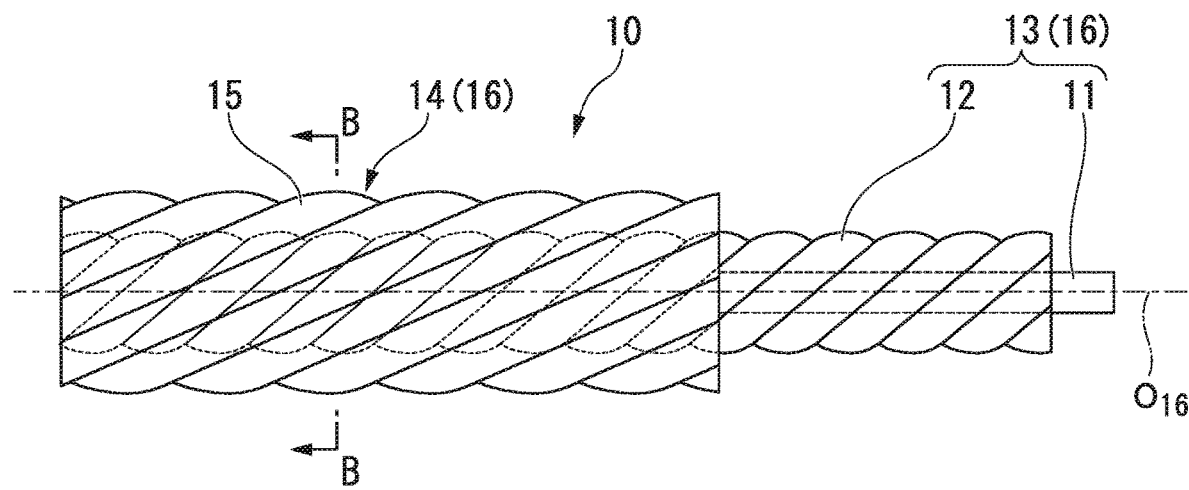
FIG. 3 is a schematic front view showing a constituent example of a wire for a medical device of the embodiment of the present invention.
Figure 4:
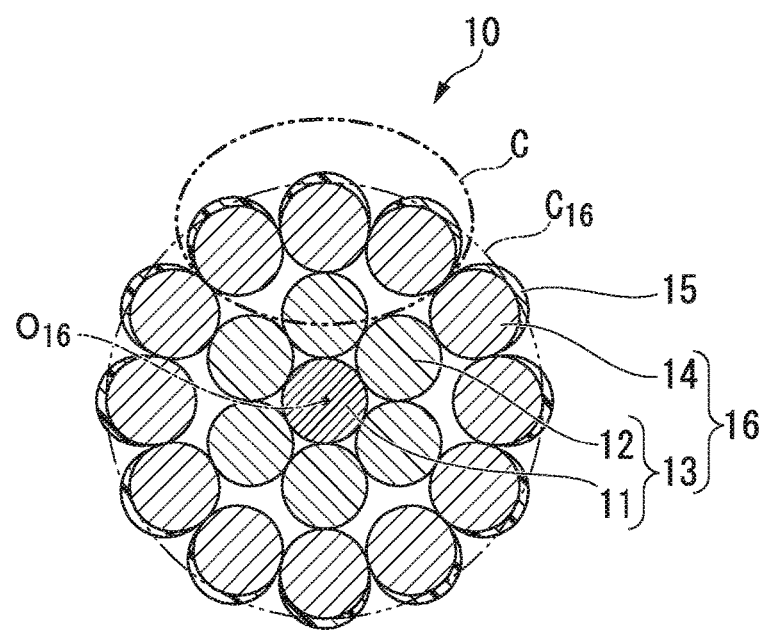
FIG. 4 is a sectional view taken along line B-B in FIG. 3.
Figure 5:
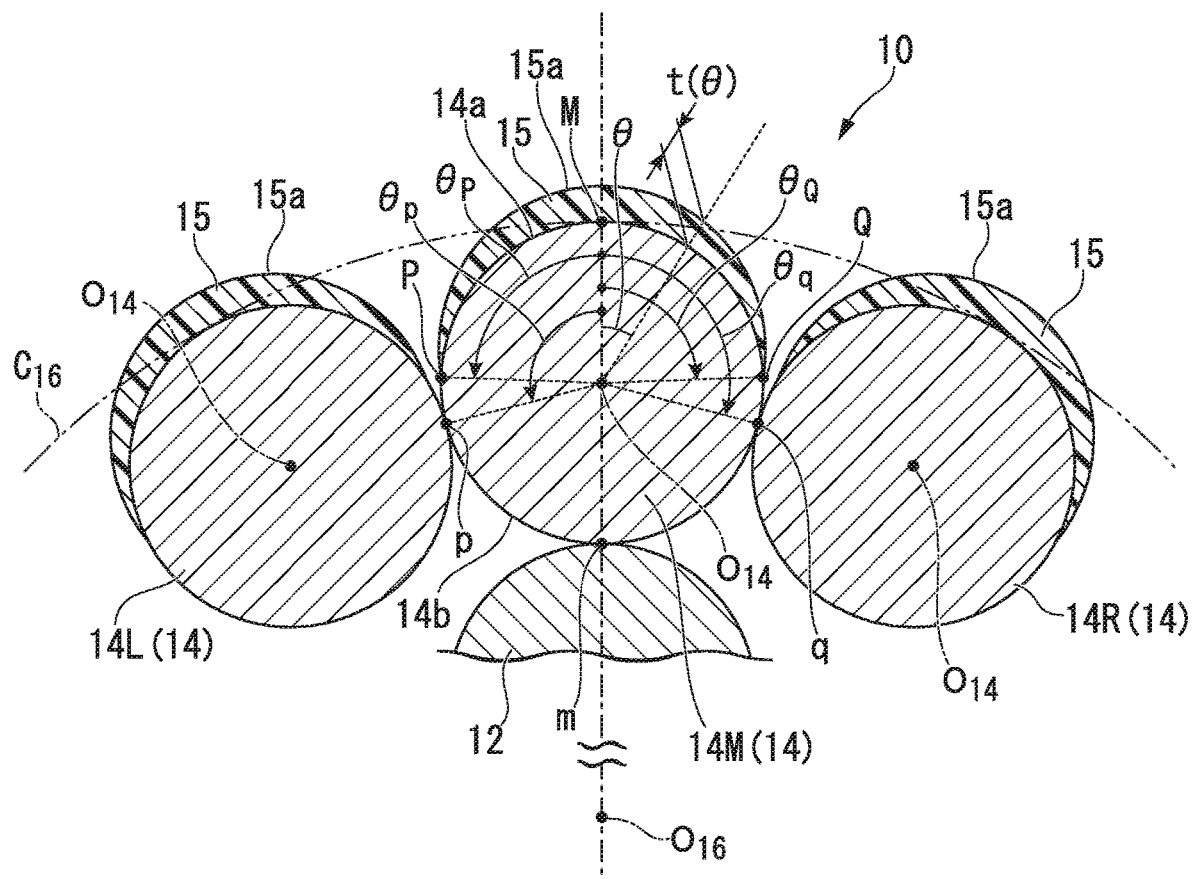
FIG. 5 is an enlarged view of a part C in FIG. 4.

FIG. 3 is a schematic front view showing a constituent example of the wire for a medical device of the embodiment of the present invention. FIG. 4 is a sectional view taken along line B-B in FIG. 3. FIG. 5 is an enlarged view of a part C in FIG. 4.

As shown in FIGS. 3 and 4, the manipulation wire 10 includes a wire body 16 and a solid lubrication film 15.

The wire body 16 has an outer circumferential layer formed of a plurality of twisted metal strands. A constitution inside the outer circumferential layer of the wire body 16 is not limited. As an example of the wire body 16 in the present embodiment, 1×19 stranded wire as shown in FIG. 4 may be used.

In the wire body 16, one core strand 11, six first strands 12, and twelve second strands 14 (a plurality of metal strands, outer circumferential layer) are twisted.

The core strand 11 is a metal strand that extends along a central axis $O_{16}$ of the wire body 16.

The first strands 12 are metal strands that are twisted on an outer circumferential portion of the core strand 11. The core strand 11 and the six first strands 12 constitute 1×7 strand 13. A twisting direction of the first strands 12 is not limited. In the example shown in FIG. 3, the twisting direction of the first strands 12 is an S twist.

The second strands 14 are metal strands that are twisted to be adjacent in a circumferential direction on an outer circumferential portion of the strand 13. A twisting direction of the second strands 14 is not limited. In the example shown in FIG. 3, the twisting direction of the second strands 14 is an S twist.

The twelve second strands 14 constitute the outer circumferential layer of the wire body 16.

In FIG. 5 that schematically shows a cross section perpendicular to the central axis $O_{16}$, second strands 14L, 14M, and 14R aligned in a circumferential direction among the second strands 14 are shown. In the following description, how the second strand 14M is selected is arbitrary.

Sine the manipulation wire 10 is a stranded wire, sectional shapes of the first strands 12 and the second strands 14 in a cross section perpendicular to the central axis $O_{16}$ are strictly ellipses. In the sectional view of FIG. 4. FIG. 5 or the like, the sectional shapes of the first strands 12 and the second strands 14 are schematically represented by circles.

In the following description of a sectional shape of the wire body 16, there is no need to strictly distinguish the sectional shapes of the metal strands between an ellipse and a circle. Thus, for simplicity, in the following description, an elliptical cross section is regarded as approximately a circular cross section. For this reason, with regard to, for example, the sectional shapes of the second strands 14, terms such as "circular arcs," "circular are shapes," "major arcs." "minor arcs" or the like may be used.

This description is only approximately exact description in the cross section perpendicular to the central axis $O_{16}$, but is exact description in a cross section perpendicular to a central axis $O_{14}$.

As shown in FIG. 5, the second strand 14M is in contact with the other second strands 14L and 14R adjacent to each other at points p and q (contact portions) in a circumferential direction. Therefore, the second strand 14M is in line contact with the other second strands 14L and 14R in a longitudinal direction.

Intersections between a straight line connecting the central axis $O_{16}$ and the central axis $O_{14}$ of the second strand 14M and a surface of the second strand 14M are represented as points M and m in the order of increasing distance from the central axis $O_{16}$.

In the second strand 14M, an area of a circular arc pMq that is a major arc is referred to as an outer circumference-side surface (an outside exposure surface) 14a, and an area of a circular arc pmq that is a minor arc is referred to as an inner circumference-side surface 14b. Similarly, the outer circumference-side surface 14a and the inner circumference-side surface 14b are defined in each of the second strands 14.

Each of the outer circumference-side surfaces 14a in the second strands 14 is formed as an outside exposed surface that is exposed outside when the wire body 16 is viewed in a radial direction directed to the central axis $O_{16}$.

Among the core strand 11, the first strands 12, and the second strands 14, all may have the same strand diameter, or at least some may have different strand diameters. In the examples shown in FIGS. 3 and 4, the strand diameters of the core strand 11, the first strands 12, and the second strands 14 are identical to one another by way of example. For this example, as shown in FIG. 3, the wire body 16 is formed of a cross lay strand.

Materials of the core strand 11, the first strands 12, and the second strands 14 may be different or the same.

For example, in a specific example of the wire body 16, SUS403 having a diameter of 0.15 mm may be used as each of the core strand 11, the first strands 12, and the second strands 14. In this case, a wire diameter of the wire body 16 is 0.7 mm.

To improve slidability of the surface of the wire body 16, the solid lubrication film 15 is formed on each of the outer circumference-side surfaces 14a of the second strands 14. In the present embodiment, the solid lubrication film 15 is formed on the entire wire body 16 in a longitudinal direction.

However, the solid lubrication film 15 may be formed only at necessary portions in order to improve the slidability on the surface of the wire body 16. That is, in the case where a portion sliding on a contact target on the surface of the wire body 16 are limited, or in the case where sliding resistance is lower than or equal to an allowable value, a formation range of the solid lubrication film 15 may be reduced. For example, the solid lubrication film 15 may be formed on a surface of a partial section of the wire body 16 in the longitudinal direction. For example, the solid lubrication film 15 may be formed only on some of the plurality of second strands 14 constituting the outer circumferential layer of the wire body 16.

As shown in FIG. 5, in the present embodiment, the solid lubrication film 15 is discontinuous across the contact portion between the second strands 14 in a circumferential direction.

A point P of an end of the solid lubrication film 15 which is close to the second strand 14L is located closer to a point M than a point p. A point Q of an end of the solid lubrication film 15 which is close to the second strands 14R is located closer to the point M than a point q. An angle measured around the central axis $O_{14}$ on the basis of a line segment $O_{14}M$ is expressed as θ. An shown clockwise direction is referred to as a positive direction, and an shown counterclockwise direction is referred to as a negative direction. A position of the point M is θ=0.

Positions of the points p, P, Q and q are represented as angle $-\theta_p$, $-\theta_P$, $\theta_Q$, and $\theta_q$, provided that $0<\theta_P<\theta_p$, and $0<\theta_Q<\theta_q$.

The solid lubrication film 15 is formed within an area of a circular arc PMQ on the outer circumference-side surface 14a.

In the present embodiment, a thickness t(θ) of the solid lubrication film 15 has a maximum value $t_0$ when θ=0, and a minimum value 0 when $\theta=-\theta_P$ and $\theta=\theta_Q$. Here, the thickness is a thickness measured from the outer circumference-side surface 14a in the radial direction of the second strand 14M.

Since the portion of θ=0 is a portion that constitutes a maximum outer diameter of the wire body 16, a maximum pressing force tends to be generated when the portion of θ=0 comes into contact with an inner circumferential surface of the coil sheath 4. For this reason, the thickness $t_0$ is more preferably a maximum thickness in each of the solid lubrication films 15.

However, in the case where slidability and strength of resistance to the contact target with the solid lubrication film 15 are obtained, the thickness of the solid lubrication film 15 may not be a maximum at the portion of θ=0. A change of the thickness t(θ) is not limited to a monotonous change as shown in FIG. 5.

In the cross section perpendicular to the central axis $O_{16}$ of the wire body 16, a minimum virtual circle in which the second strands 14 constituting the outer circumferential layer are included is assumed to be a circle $C_{16}$. In the example shown in FIG. 5, the circle $C_{16}$ centers on the central axis $O_{16}$, and becomes a circumscribed circle of the wire body 16 in which the points M of the second strands 14 are contacts. Hereinafter, the "cross section perpendicular to the central axis $O_{16}$ of the wire body 16" may be used as a "perpendicular cross section."

The solid lubrication film 15 is distributed inside and outside the circle $C_{16}$ in the perpendicular cross section. In the solid lubrication film 15, when a line of intersection between the perpendicular cross section and a surface 15a of the solid lubrication film 15 is referred to as an outer edge of the solid lubrication film 15, a part of the outer edge of the solid lubrication film 15 of the perpendicular cross section is inside the circle $C_{16}$.

Furthermore, when the size (a cross-sectional area) of a portion outside the circle $C_{16}$ in the perpendicular cross section is $A_{15}$, and the size (a cross-sectional area) of a portion inside the circle $C_{16}$ is $B_{15}$, the solid lubrication film 15 satisfies $A_{15}/B_{15} > 0.7$.

Figure 14:
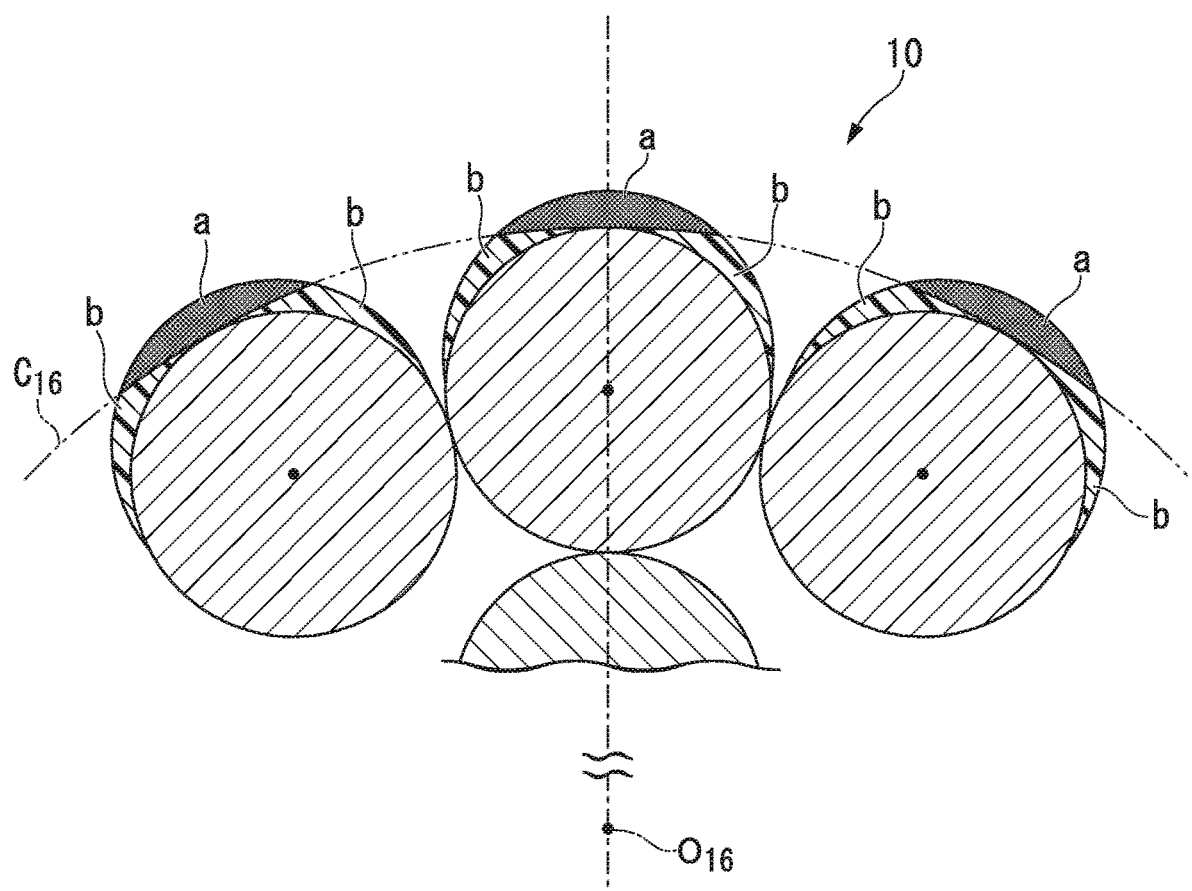
FIG. 14 is an enlarged view of a part C in FIG. 4.

FIG. 14 is a view in which several reference signs are omitted from the sectional view shown in FIG. 5 and hatching of a part of the solid lubrication film 15 is changed. Components shown in FIG. 14 are the same as those shown in FIG. 5. In FIG. 14, a portion a indicates a portion of the solid lubrication film 15 which is outside the circle $C_{16}$, and a portion b indicates a portion of the solid lubrication film 15 which is inside the circle $C_{16}$. When the total sizes (cross-sectional areas) of the portions a for all of the second strands 14 is $A_{15}$, and the total sizes (cross-sectional areas) of the portions b for all of the second strands 14 is $B_{15}$, the solid lubrication film 15 satisfies $A_{15}/B_{15} > 0.7$ in the cross section perpendicular to the central axis $O_{16}$ of the wire body 16 in a section of at least a part of the wire body 16 in a longitudinal direction.

A material of the solid lubrication film 15 is not limited as long as it is a solid material capable of reducing sliding friction between the solid lubrication film 15 and the contact target.

For example, a constitution in which a film is formed by mixing a lubricativity imparting substance of a solid phase with a primer adhering to the second strands 14 is also used as the solid lubrication film 15.

In this case, examples of the primer include a polyamide-imide resin, an epoxy resin, a polyethersulfone resin, and so on. Examples of the lubricativity imparting substance of a solid phase include particles of a fluorine resin, a silicone resin, molybdenum disulfide, carbon, and the like. The particle size of the particle of the lubricativity imparting substance may be, for example, 0.1 μm or more and 1 μm or less.

A polytetrafluoroethylene (PTFE) resin may be used as the fluorine resin.

A constitution of a multilayered film in which a film is formed by mixing the lubricativity imparting substance of a solid phase with the primer as described above and furthermore the lubricativity imparting substance is superimposed on the film may be used as the solid lubrication film 15.

For example, since the PTFE that is the lubricativity imparting substance can be fused to form a coating when heated to about 380° C., the PTFE is also suitable to be used as a layered film superimposed on the film formed by mixing the lubricativity imparting substance of a solid phase with the primer as described above.

The manipulation wire 10 is manufactured by forming the wire body 16 using a well-known manufacturing method and forming the solid lubrication film 15 on each of the outer circumference-side surfaces 14a of the wire body 16 outer circumference-side surface 14a.

The manufacturing method of the solid lubrication film 15 is not limited.

For example, the solid lubrication film 15 may be manufactured by applying an uncured paint acting as the solid lubrication film 15 so as not to be penetrated in the vicinity of a contact portion of each of the second strands 14 in the circumferential direction (hereinafter referred to simply as a contact portion) and then curing the paint. To apply the paint so as not to be penetrated in the vicinity of the contact portion, for example a paint layer having high viscosity may be formed on a working plane, and the wire body 16 may be rolled on the paint layer.

For example, the solid lubrication film 15 may be manufactured by applying an uncured paint acting as the solid lubrication film 15 to the outer circumferential portion of the wire body 16, and curing the paint in a state in which the paint around the contact portion is removed. To remove the applied paint from the contact portion in the circumferential direction and its neighborhood, for example the wire body 16 may rotate about the central axis $O_{16}$. In this case, since the paint moves outward along the outer circumference-side surfaces 14a in a radial direction due to an action of a centrifugal force caused by the rotation of the wire body 16, the paint is removed from the neighborhood of the contact portion.

For example, the solid lubrication film 15 may be manufactured by applying a paint to the entire outer circumferential portion of the wire body 16 and removing the paint around the contact portion after or while the paint is cured using mechanical or chemical means.

For example, the solid lubrication film 15 may be manufactured by filling only the neighborhood of the contact portion with a compound such as carbon, applying a paint, curing the paint, and removing the compound and a paint film on the compound using a chemical solution.

Next, an operation of the endoscopic device 1 will be described focusing on an operation of the manipulation wire 10.

Figure 6:
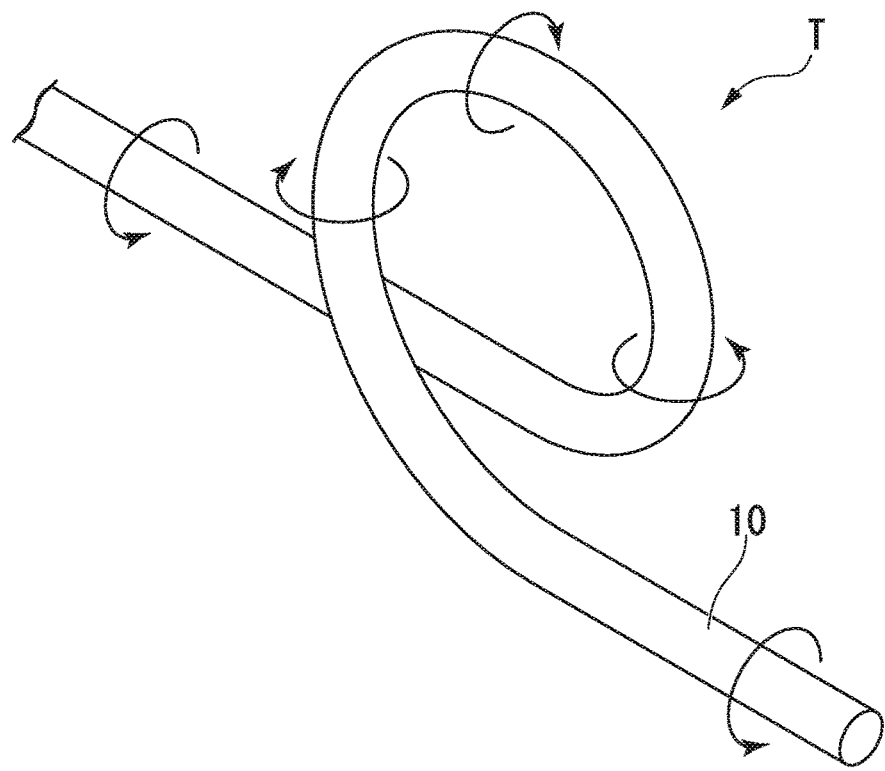
FIG. 6 is a view showing a schematic operation of the wire for the medical device of the embodiment of the present invention.
Figure 7:
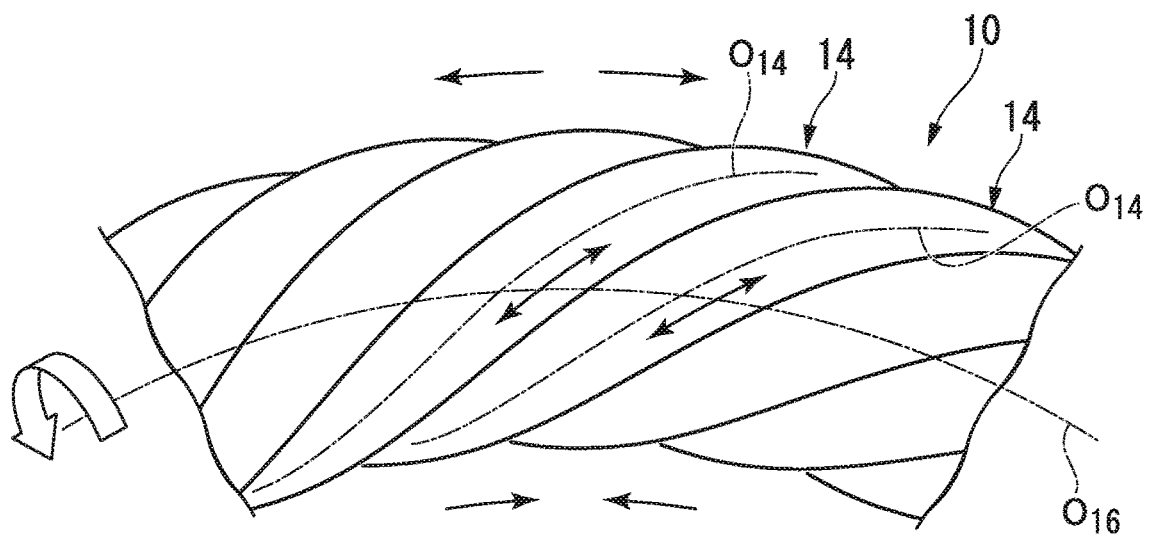
FIG. 7 is a schematic view showing an operation of the wire for the medical device of the embodiment of the present invention.

FIG. 6 is a schematic operation view showing the wire for the medical device of the embodiment of the present invention. FIG. 7 is a schematic view showing an operation of the wire for the medical device of the embodiment of the present invention.

An operator can advance/retract the manipulation wire 10 in the coil sheath 4 along the central axis $O_{16}$ by advancing/retracting the slider 5c of the endoscopic device 1 on the slide shaft 5*d*. In this case, the central axis O$_{16}$ of the manipulation wire 10 is bent by following the coil sheath 4 when the coil sheath 4 is bent.

The clip 2 of the endoscopic device 1 is advanced/retracted with respect to the pushing tube 3 depending on forward/backward movement of the manipulation wire 10 in a state in which the clip 2 does not grip the gripping target. Before the operator inserts the endoscopic device 1 into the body of a patient, the operator pulls the manipulation wire 10 to some extent, and draws the clip 2 into the pushing tube 3. For example, the operator inserts the distal end of the coil sheath 4 of the endoscopic device 1 into the endoscope channel or the like of the endoscope that has been inserted into the body of the patient in advance. The operator moves the entire manipulator 5 in an inserting direction, and thereby causing the distal end of the coil sheath 4 to extend from the endoscope channel. The operator adjusts an amount of insertion of the endoscopic device 1, and moves the pushing tube 3 and the clip 2 located at the distal end of the coil sheath 4 into the body of the patient for which gripping by the clip 2 is required.

In this case, the coil sheath 4 and the manipulation wire 10 inside the coil sheath 4 are bent according to a bend of the endoscope channel. For example, as shown in FIG. 6, a spiral loop-like bent portion T may be formed at the manipulation wire 10 depending on an insertion portion of the endoscope.

The operator moves the slider 5*c* in a direction directed from its proximal end toward its distal end in a state in which a position of the slide shaft 5*d* of the manipulator 5 is fixed in order to extrude the clip 2 from the pushing tube 3. The manipulation wire 10 moves toward the distal end in the coil sheath 4 depending on an amount of movement of the slider 5*c*. In this case, the manipulation wire 10 slides on the inner circumferential surface of the coil sheath 4 in an axial direction. Since the solid lubrication film 15 is formed on the outer circumferential portion of the manipulation wire 10, a sliding load of the manipulation wire 10 against the coil sheath 4 is reduced, compared to the case where the solid lubrication film 15 is not formed.

The clip 2 seized on the engaging portion 10*a* of the manipulation wire 10 is extruded from the pushing tube 3 toward the inside of the body. As shown in FIG. 2, the clip 2 extruded from the pushing tube 3 is opened in a V shape by its own elastic restoring force.

The operator makes the clip 2 closer to the gripping target, for example, by combining bending manipulation of the endoscope and movement of the entire endoscopic device 1 while watching an image photographed by the endoscope. Afterward, the operator rotatably manipulates the endoscopic device 1 so as to enable the clip 2 to grip tissue (for example, a blood vessel) of the gripping target. That is, the operator rotates the rotary grip 5*b* of the manipulator 5 around the central axis of the slide shaft 5*d*, and rotates the proximal end of the manipulation wire 10 around the central axis O$_{16}$. Thereby, the clip 2 is rotated about the central axis O$_{16}$ depending on the amount of rotation of the distal end of the manipulation wire 10.

After the clip 2 is disposed in a posture in which the gripping target is sandwiched between the gripping portions 2*a*, the operator moves the slider 5*c* toward the proximal end, and pulls the manipulation wire 10 toward the proximal end. The clip 2 is drawn in the pushing tube 3, and the gripping target is gripped by the clip 2. Since the portions of the gripping portions 2*a* drawn in the pushing tube 3 press the inner circumferential surface of the pushing tube 3 by the elastic restoring force, the clip 2 is seized on the pushing tube 3 so as not to be pulled out.

After the operator watches the image of the endoscope and can confirm that the gripping target is properly gripped, the operator further moves the slider 5*c* toward the proximal end. Thereby, the engaging portion 10*a* is removed from the clip 2. In this way, the clip 2 gripping the gripping target and the pushing tube 3 are separated from the manipulation wire 10, and are placed in the body of the patient in a state in which the clip 2 has gripped the gripping target.

Since the manipulation wire 10 is the stranded wire obtained by twisting the metal strands, the manipulation wire 10 has high torsional rigidity. For this reason, the manipulation wire 10 can transmit a rotational driving force caused by rotation of the rotary grip 5*b* which is close to the proximal end of the manipulation wire 10 to the vicinity of the distal end of the manipulation wire 10 in the aforementioned operation.

In this case, the manipulation wire 10 slides on the inner circumferential surface of the coil sheath 4 in the circumferential direction. Since the solid lubrication film 15 is formed at the outer circumferential portion of the manipulation wire 10, the sliding load of the manipulation wire 10 against the coil sheath 4 is reduced, compared to the case where the solid lubrication film 15 is not formed.

However, like the bent portion T shown in FIG. 6, when the manipulation wire 10 is greatly bent, driving torque required for the rotational manipulation increases to receive greater resistance, compared to the case where the manipulation wire 10 is not bent. This point will be described below.

As shown in FIG. 7, when the manipulation wire 10 is bent, tensile stress occurs at a convex bent portion (on an upper side of FIG. 7) due to bending deformation, and compression stress occurs at a concave bent portion (on a lower side of FIG. 7).

In this state, like the shown outline arrow, when the manipulation wire 10 is rotated about the central axis O$_{16}$, a tensile region and a compression region are gradually replaced at the outer circumferential portion of the manipulation wire 10 in association with the rotation. For example, when the entire manipulation wire 10 is rotated by half, the manipulation wire 10 of the bent portion becomes the same as receiving bending deformation by which it is bent from an initial bent state to the exact opposite bent state.

That is, for a work required to rotate the manipulation wire 10 in the bent coil sheath 4, a work for bending the manipulation wire 10 depending on an amount of rotation is added to a work for performing torsional deformation on the manipulation wire 10 against a friction from the coil sheath 4.

Since the solid lubrication film 15 is formed at a portion where the manipulation wire 10 slides on the coil sheath 4, the sliding friction is reduced.

Furthermore, the solid lubrication film that comes into close contact with both of the outer circumference-side surfaces 14*a* is not formed around the contact portion between the second strands 14 adjacent to each other in the manipulation wire 10.

As a result, the contact portion between the second strands 14 adjacent to each other is in contact in a state in which the second strands 14 are relatively movable along surfaces thereof.

As shown in FIG. 7, since the second strands 14 are disposed in an oblique direction in which they intersect the central axis O$_{16}$, when a tensile or compression external force is applied in a direction parallel to the central axis O$_{16}$, the second strands 14 cause shear displacement in an axial direction thereof (see the shown bidirectional arrow). Thereby, stress occurring at the outer circumferential layer of the manipulation wire 10 is relieved.

In this way, since the outer circumferential layer of the manipulation wire 10 has a degree of freedom of the shear displacement of the second strands 14, flexibility of the manipulation wire 10 increases, compared to a round bar-like elastic body having the same diameter and the same material. That is, an external force required to bend the manipulation wire 10 is smaller than that required to bend the round bar-like elastic body having the same diameter and the same material.

Here, the operation of the manipulation wire 10 will be described in comparison with a wire 110 of a comparative example.

Figure 8:
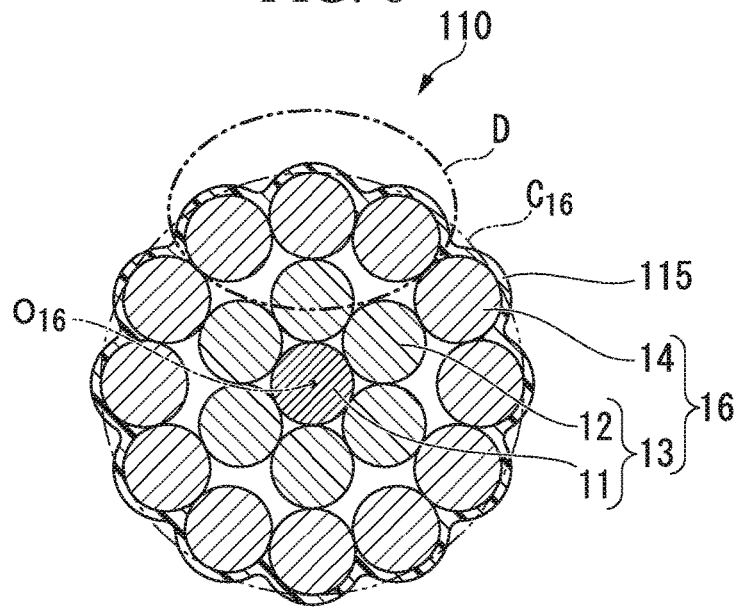
FIG. 8 is a schematic sectional view of a wire of a comparative example.
Figure 9:
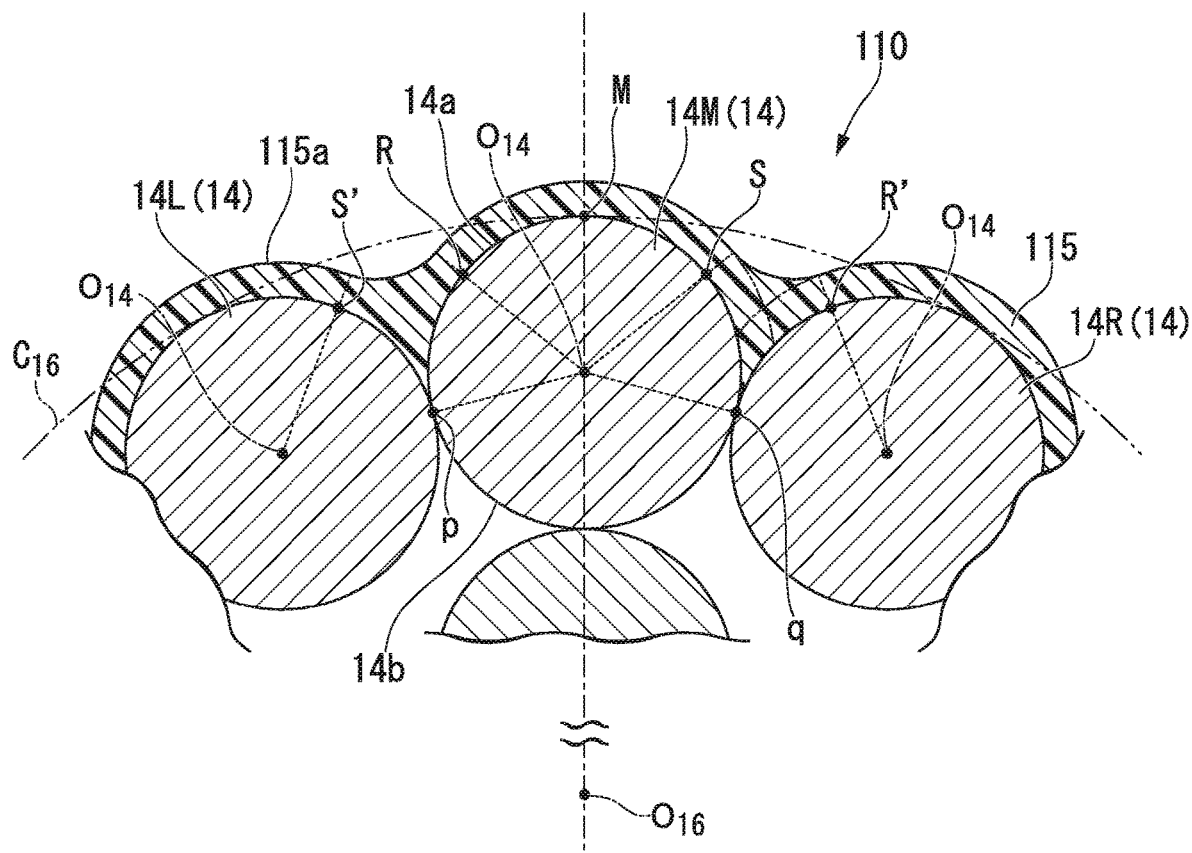
FIG. 9 is an enlarged view of a part D in FIG. 8.

FIG. 8 is a schematic sectional view of a wire of a comparative example. FIG. 9 is an enlarged view of a part D in FIG. 8.

As shown in FIG. 8, a wire 110 of a comparative example includes a solid lubrication film 115 instead of the solid lubrication film 15 of the manipulation wire 10.

The solid lubrication film 115 is formed of the same material as the solid lubrication film 15. However, the solid lubrication film 115 is formed by nearly uniformly applying the same uncured paint as that of which the solid lubrication film 15 is formed to the entirety of each outer circumference-side surface 14a of a wire body 16 and curing the paint.

Therefore, as shown in FIG. 9, the solid lubrication film 115 has a thickness $t_0$ within an area of a circular arc RMS on an outer circumference-side surface 14a of a second strand 14M.

A wedged region between a circular arc pR (Sq) of the second strand 14M and a circular arc pS' (qR') of a second strands 14L (14R) which is opposite to the circular arc pR (Sq) is filled with the solid lubrication film 115.

In the wire 110, the solid lubrication film 115 of the region interposed between the circular arc pR and the circular arc pS' (the circular arc Sq and the circular arc qR') in a circumferential direction is formed in a shape in which a thickness is thicker than or equal to the thickness $t_0$ by a surface tensile force of the paint for forming the solid lubrication film 115.

That is, in the wire 110 of the comparative example, second strands 14 adjacent to each other in the circumferential direction are mutually adhered by the wedged solid lubrication film 115 having a thickness that is thicker than the thickness $t_0$ of the solid lubrication film 115 that is formed at an outermost circumferential portion of the wire body 16 by curing the paint penetrated around a contact portion in a wedged shape.

In the solid lubrication film 115, when a line of intersection between a perpendicular cross section and a surface 115a of the solid lubrication film 115 is referred to as an outer edge of the solid lubrication film 115, a part of the outer edge of the solid lubrication film 115 of the perpendicular cross section is inside a circle $C_{16}$ like the aforementioned solid lubrication film 15. However, when the size (a cross-sectional area) of a portion outside the circle $C_{16}$ in the perpendicular cross section is $A_{115}$, and the size (a cross-sectional area) of a portion inside the circle $C_{16}$ is $B_{115}$, the solid lubrication film 115 satisfies $A_{115}/B_{115} \leq 0.7$.

With this constitution, since the second strands 14 of the outer circumferential layer of the wire 110 are integrally fixed by the solid lubrication film 115 around the contact portion, shear displacement of the second strands 14 adjacent to each other is inhibited. As a result, in comparison with the manipulation wire 10 of the present embodiment, the wire 110 is deteriorated in flexibility.

Despite the fact that the wire 110 includes the solid lubrication film 115 formed of the same material as the solid lubrication film 15 on the outer circumferential portion thereof, a manipulating force for rotation is further increased when a rotational driving force is transmitted in a bent state.

For this reason, in the case where a bending amount in the wire 110 is great, rotational driving may become difficult. Since a driving load is great even if the wire 110 can be rotatably driven, a rotation flip occurs easily, and smooth continuous rotational driving may become impossible.

According to the manipulation wire 10 of the present embodiment, problems as in the wire 110 of the comparative example are inhibited.

To verify the effects of the manipulation wire 10, the inventors of the present invention experimentally produced the manipulation wire 10 and the wire 110 and performed evaluation.

Figure 10:
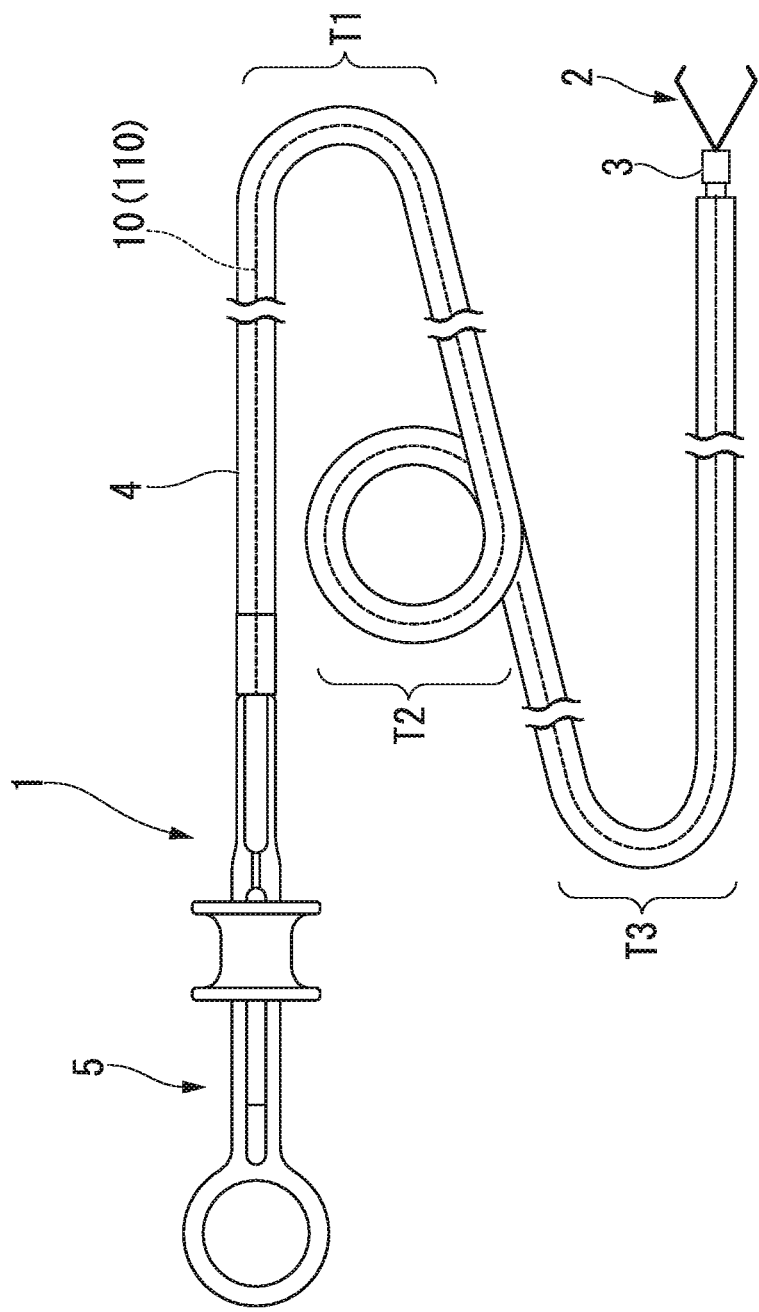
FIG. 10 is a schematic view showing a testing method of the wire for the medical device of the embodiment of the present invention.

FIG. 10 is a schematic view showing a testing method for the wire for the medical device of the embodiment of the present invention.

In a preproduction sample of the manipulation wire 10, an SUS403 wire having a diameter of 0.15 mm was used for any of the core strand 11, the first strands 12, and the second strands 14.

Polyflon (registered trademark) EK-1909 (product name, commercially available from Daikin Koyo Co.) was used as the primer for the solid lubrication film 15. PTFE particles having distribution in which a particle size of 0.1 μm or more and 1 μm or less were used as the lubricativity imparting substance of the solid lubrication film 15.

The thickness $t_0$ of the solid lubrication film 15 was set to 10 μm. As described above, in thickness distribution of the solid lubrication film 15, a thickness became a maximum value $t_0$ at the point M, was reduced from the point M toward the points P and Q, and reached 0 μm at the points P and Q. The lengths of the circular arc Pp and the circular arc Qq that were regions in which the solid lubrication film 15 was not formed were about 0.02 mm. As a result, the cross-sectional area of the solid lubrication film 15 in the perpendicular cross section satisfied the relation of $A_{15}/B_{15} > 0.7$.

A preproduction sample of the wire 110 was formed by applying the same paint as that of which the solid lubrication film 115 was formed to the entire outer circumferential surface of the same wire body 16 as the manipulation wire 10. The solid lubrication film 15 as described above was formed on the outer circumferential portion of the wire 110. A thickness of the solid lubrication film 115 at the point M was set to $t_0$. The solid lubrication film 115 exceeding the thickness $t_0$ was formed between the second strands 14 of the wire 110. As a result, the cross-sectional area of the solid lubrication film 115 in the perpendicular cross section satisfied the relation of $A_{115}/B_{115} \leq 0.7$.

Evaluation of each of the preproduction samples was performed in a state in which the sample was assembled with the endoscopic device 1 and the coil sheath 4 having a full length of 2000 mm was bent. As evaluation points, measurement of a force amount transmission rate and check of presence/absence of rotation flip were performed.

The coil sheath 4 was bent in an approximate Z shape as a whole by a restraint jig (not shown) and bent portions T1 and T3 that were bent with a radius of curvature of 100 mm as shown in FIG. 10. Furthermore, a bent portion T2 bent in a loop shape having a radius of curvature of 100 mm was formed between the bent portions T1 and T3 of the coil sheath 4.

The measurement of the force amount transmission rate was performed by extruding the wire in a state in which the coil sheath 4 was bent by the restraint jig as described above, and measuring an extrusion force amount of the wire using a load cell.

The force amount transmission rate of the preproduction sample of the manipulation wire 10 was 65%. In contrast, the force amount transmission rate of the preproduction sample of the wire 110 was 44%.

As a result, if necessary rotational driving forces were the same, the manipulation wire 10 had a small input force amount requested for rotational manipulation, and thus it was understood that the rotational manipulation was performed with a lighter load.

The rotation flip did not occur at the preproduction sample of the manipulation wire 10. Since the clip 2 was rotated while well following up rotation of the rotary grip 5b, a posture of the clip 2 was easily adjusted.

In contrast, the rotation flip occurred at the preproduction sample of the wire 110. Even if the rotary grip 5b was rotated, the clip 2 was not rotated while smoothly following up the rotation of the rotary grip 5b. Thus, a shortage of rotation and excessive rotation occurred, and the posture of the clip 2 could not be adjusted.

As described above, since the solid lubrication films 15 were discontinuously formed across the contact portion between the second strands 14 adjacent to each other in the circumferential direction in the manipulation wire 10, the manipulation wire 10 has slidability for a member of a contact target, and can smoothly transmit rotation about the axis in a bent state.

According to the endoscopic device 1 using the manipulation wire 10, due to the use of the manipulation wire 10, even if the manipulation wire 10 is bent, a smooth operation becomes possible by the forward/backward movement and the rotation of the manipulation wire 10.

[First Modification]

Next, a first modification of the above embodiment will be described.

Figure 11:
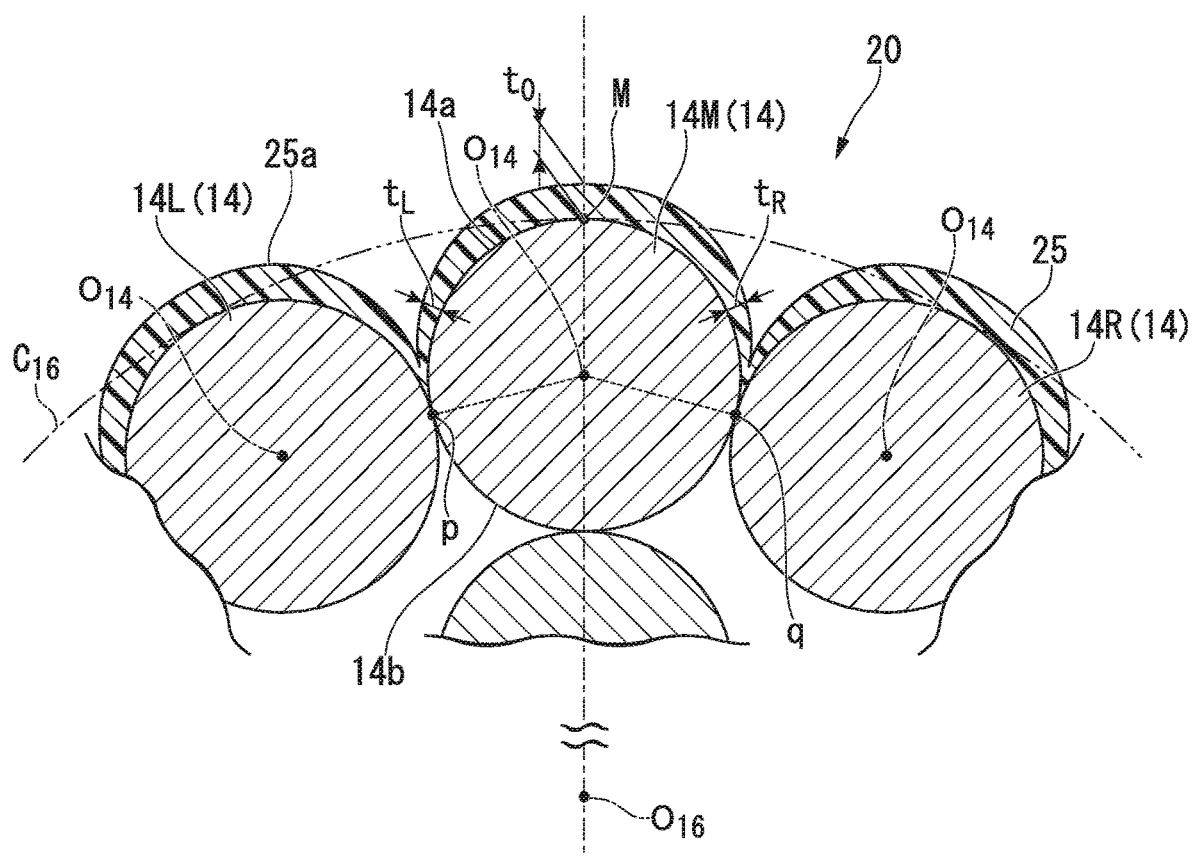
FIG. 11 is a schematic partial sectional view showing a constituent example of a wire for a medical device of a first modification of the embodiment of the present invention.

FIG. 11 is a schematic sectional view showing a constituent example of a wire for a medical device of a first modification of the embodiment of the present invention.

As shown in FIG. 2, a treatment tool (a medical device) 1A of this modification includes a manipulation wire (a wire for a medical device) 20 of this modification instead of the manipulation wire 10 of the endoscopic device 1 of the above embodiment.

Hereinafter, a difference from the above embodiment will be mainly described.

As shown in FIG. 11 in a partial cross section, the manipulation wire 20 includes a solid lubrication film 25 instead of the solid lubrication film 15 of the manipulation wire 10 of the above embodiment.

In FIG. 11, second strands 14L and 14M adjacent to each other are shown, but the solid lubrication film 25 is formed by covering all outer circumference-side surfaces 14a of the second strands inclusive of the other second strands 14 that are not shown.

The solid lubrication film 25 is formed on an entire outside exposure surface of a wire body 16. Points p and q, each of which is a contact portion between the neighboring second strands 14, is covered by the solid lubrication film 25. In the solid lubrication film 25, when a line of intersection between a perpendicular cross section and a surface 25a of the solid lubrication film 25 is referred to as an outer edge of the solid lubrication film 25, a part of the outer edge of the solid lubrication film 25 of the perpendicular cross section is inside a circle $C_{16}$.

However, unlike the solid lubrication film 115 of the aforementioned comparative example, when the size (a cross-sectional area) of a portion outside the circle $C_{16}$ in the perpendicular cross section is $A_{25}$, and the size (a cross-sectional area) of a portion inside the circle $C_{16}$ is $B_{25}$, the solid lubrication film 25 satisfies $A_{25}/B_{25}>0.7$.

This constitution is obtained, for example, as a thickness of the solid lubrication film 25 within an appropriate range inside the circle $C_{16}$ is thinner than the thickness at the portion outside the circle $C_{16}$. For example, in the example shown in FIG. 11, thicknesses $t_L$ and $t_R$ of portions close to the points p and q inside the circle $C_{16}$ are smaller than the thickness $t_0$ at a point M.

As described in the comparative example (see FIG. 9) of the above embodiment, when the second strands 14 adjacent to each other are closely adhered around the contact portion by the solid lubrication film having a large thickness, the flexibility as that of the wire may be reduced compared to the manipulation wire 10 of the above embodiment, and the rotational manipulation may not be smoothly performed.

However, since this modification satisfies $A_{25}/B_{25}>0.7$, a thickness of the solid lubrication film 25 formed between the second strands 14 adjacent to each other inside the circle $C_{16}$ (hereinafter referred to as "interstrand") is thinner compared to the aforementioned comparative example.

As a result of intensive studies of the inventors, in the case where the interstrand thickness is thin to some extent, an amount of reduction of the flexibility of the stranded wire is within an allowable range. It is thought that the reason is that, when the interstrand thickness is thin to some extent, the interstrand solid lubrication film 25 is easily broken even with a low force amount, and thereby the second strands 14 adjacent to each other can move relative to each other when bent.

The thickness of an interstrand layered portion, that is, the length of the solid lubrication film 25 interposed between the neighboring outer circumference-side surfaces 14a in a wedged shape in a circumferential direction is determined to satisfy necessary characteristics of the manipulation wire 20 evaluated by, for example, the force amount transmission rate, the rotation flip, and so on. To be specific, a relation between the thickness of the interstrand layered portion and the necessary characteristics of the manipulation wire 20 is adjusted by experiment or deformation simulation, and thereby the length of the solid lubrication film 25 can be determined.

The thickness of the interstrand layered portion may be, for example, 0.01 mm or less. For example, the thickness of the interstrand layered portion is more preferably 0.003 mm or less.

The manipulation wire 20 having this constitution is manufactured, for example, by applying an uncured paint, which becomes the solid lubrication film 25, to an outer circumferential portion of the wire body 16, removing the paint around the contact portions such that the solid lubrication film 25 satisfying the aforementioned conditions after the curing, and curing the paint.

The manipulation wire 20 may be manufactured by a manufacturing variation in the process of manufacturing the manipulation wire 10 of the above embodiment. For example, it is thought that, in the case where the paint is removed by a centrifugal force when the manipulation wire 10 is manufactured, the paint remains between the strands around the contact portion by a variation in viscosity of the paint, and the interstrand layered portion is formed.

Since the solid lubrication film 25 is formed between the strands, the manipulation wire 20 is somewhat reduced in flexibility compared to the manipulation wire 10 of the above embodiment. However, in the manipulation wire 20, the cross-sectional area of the solid lubrication film 25 in the perpendicular cross section satisfies $A_{25}/B_{25}>0.7$, the manipulation wire 20 has slidability for the member of the contact target like the manipulation wire 10 of the above embodiment. As a result, the manipulation wire 20 can smoothly transmit rotation about an axis even in a bent state.

According to the endoscopic device 1A using the manipulation wire 20, due to the use of the manipulation wire 20, even if the manipulation wire 20 is bent, a smooth operation becomes possible by the forward/backward movement and the rotation of the manipulation wire 20.

[Second Modification]

A second modification of the above embodiment will be described.

Figure 12:
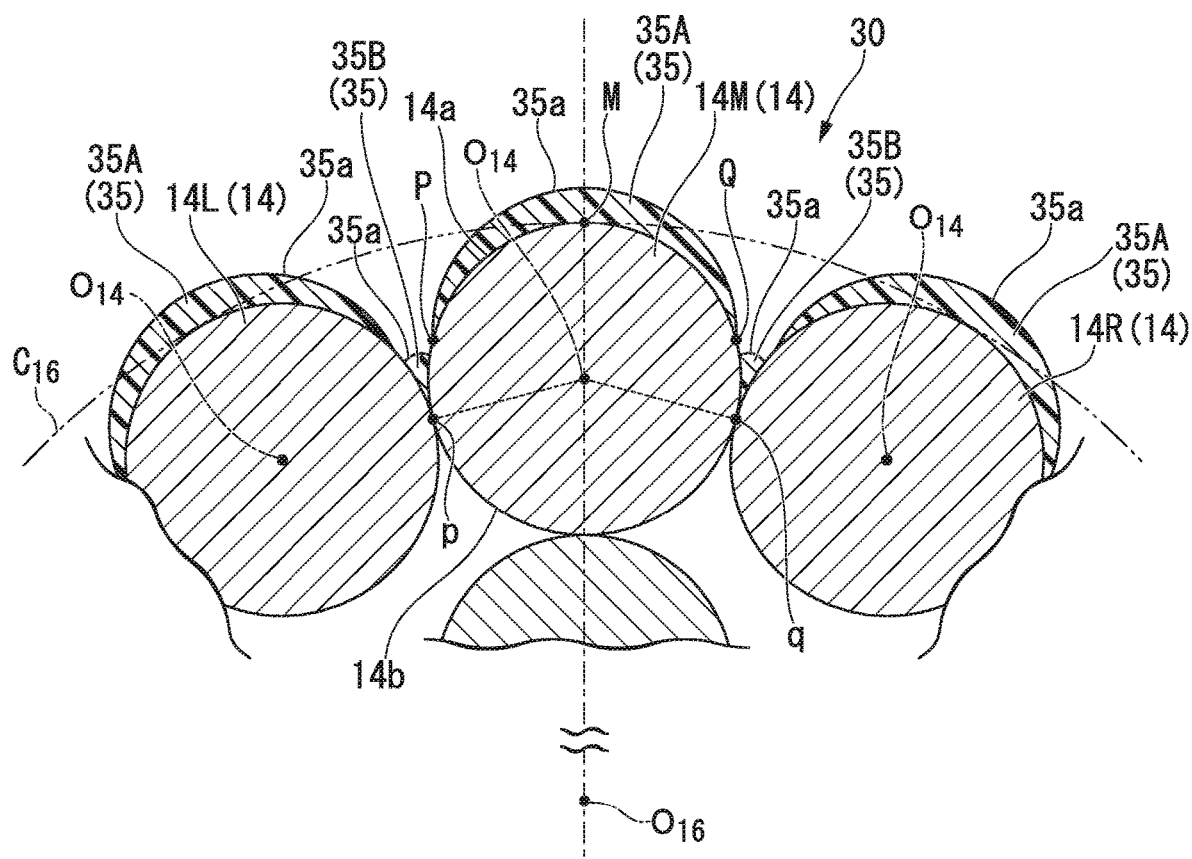
FIG. 12 is a schematic partial sectional view showing a constituent example of a wire for a medical device of a second modification of the embodiment of the present invention.

FIG. 12 is a schematic sectional view showing a constituent example of a wire for a medical device of a second modification of the embodiment of the present invention.

As shown in FIG. 2, a treatment tool (a medical device) 1B of this modification includes a manipulation wire (a wire for a medical device) 30 of this modification instead of the manipulation wire 10 of the endoscopic device 1 of the above embodiment.

Hereinafter, a difference from the above embodiment will be mainly described.

As shown in FIG. 12 in a partial cross section, the manipulation wire 30 includes a solid lubrication film 35 instead of the solid lubrication film 15 of the manipulation wire 10 of the above embodiment.

In FIG. 12, second strands 14L and 14M adjacent to each other are shown, but the solid lubrication film 35 is formed on each of the second strands 14.

The solid lubrication film 35 includes film main bodies 35A and interstrand films 35B.

Like the solid lubrication film 15 of the above embodiment, the film main bodies 35A are discontinuously formed across contact portions of second strands 14 in a circumferential direction. The film main bodies 35A are distributed inside and outside a circle $C_{16}$ in a perpendicular cross section.

Each of the interstrand films 35B covers the contact portion between second strands 14 in the perpendicular cross section in the circumferential direction, and is attached between the second strands 14 adjacent to each other in a wedged shape. Therefore, the interstrand films 35B are distributed only inside circle $C_{16}$ in the perpendicular cross section.

The film main bodies 35A and the interstrand films 35B are separated and disposed on outer circumference-side surfaces 14a of the second strands 14 in the circumferential direction.

In the solid lubrication film 35, when a line of intersection between a perpendicular cross section and a surface 35a of the solid lubrication film 35 is referred to as an outer edge of the solid lubrication film 35, a part of the outer edge of the solid lubrication film 35 of the perpendicular cross section is inside the circle $C_{16}$.

When the size (a cross-sectional area) of a portion outside the circle $C_{16}$ in the perpendicular cross section is $A_{35}$, and the size (a cross-sectional area) of a portion inside the circle $C_{16}$ is $B_{35}$, the solid lubrication film 35 satisfies $A_{35}/B_{35}>0.7$.

With this constitution, the solid lubrication film 35 is configured such that the interstrand films 35B are added to the solid lubrication film 15 of the above embodiment, and the entire solid lubrication film 35 including the interstrand films 35B satisfies $A_{35}/B_{35}>0.7$. For this reason, the thickness of the interstrand film 35B formed between the strands adjacent to each other inside the circle $C_{16}$ is thinner compared to the aforementioned comparative example.

The thickness of the interstrand film 35B between the strands, that is, the length of the interstrand film 35B interposed between the neighboring outer circumference-side surfaces 14a in a wedged shape in a circumferential direction is determined like the thickness of the interstrand layered portion in the first modification. For example, the thickness of the interstrand film 35B may be, for example, 0.01 mm or less. For example, the thickness of the interstrand film 35B is more preferably 0.003 mm or less.

In the manipulation wire 30, the solid lubrication film 35 has the film main bodies 35A like the solid lubrication film 15 in the above embodiment. Therefore, the manipulation wire 30 has slidability for the member of the contact target like the manipulation wire 10 of the above embodiment.

Since the solid lubrication film 35 has the interstrand films 35B, the manipulation wire 30 is somewhat reduced in flexibility compared to the manipulation wire 10 of the above embodiment. However, since the solid lubrication film 35 satisfies $A_{35}/B_{35}>0.7$ as a whole, the thickness of the interstrand film 35B is thinner than the interstrand layered portion in the aforementioned comparative example. As a result, the manipulation wire 30 can smoothly transmit rotation about an axis even in a bent state.

Furthermore, since the interstrand film 35B is separated from the film main body 35A, an amount of reduction of the flexibility is smaller than that of the first modification in which the solid lubrication film 25 extend between the strands.

According to the endoscopic device 1B using the manipulation wire 30, due to the use of the manipulation wire 30, even if the manipulation wire 30 is bent, a smooth operation becomes possible by the forward/backward movement and the rotation of the manipulation wire 30.

[Third Modification]

A third modification of the above embodiment will be described.

Figure 13:
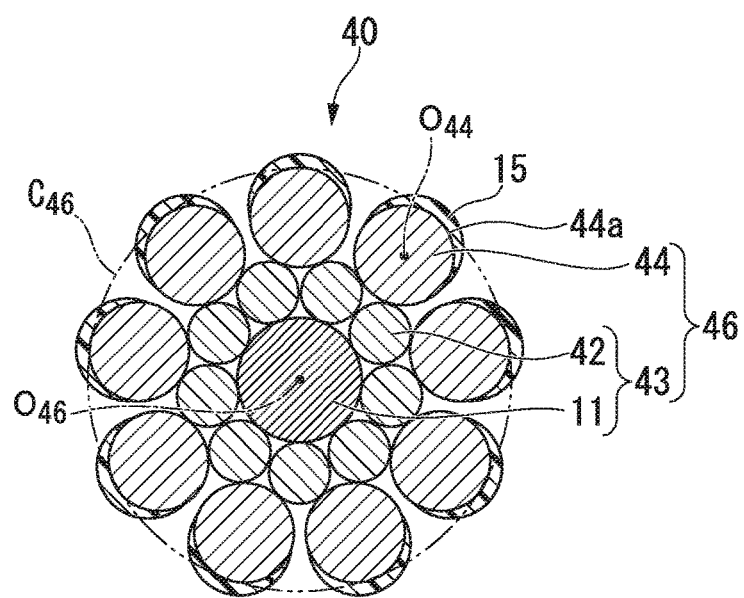
FIG. 13 is a schematic sectional view showing a constituent example of a wire for a medical device of a third modification of the embodiment of the present invention.

FIG. 13 is a schematic partial sectional view showing a constituent example of a wire for a medical device of a third modification of the embodiment of the present invention.

As shown in FIG. 2, a treatment tool (a medical device) 1C of this modification includes a manipulation wire (a wire for a medical device) 40 of this modification instead of the manipulation wire 10 of the endoscopic device 1 of the above embodiment.

Hereinafter, a difference from the above embodiment will be mainly described.

As shown in FIG. 13, the manipulation wire 40 is different from the manipulation wire 10 of the above embodiment with regard to only a wire constitution. The manipulation wire 40 includes a wire body 46 instead of the wire body 16 of the above embodiment.

In the wire body 46, a 1×19 stranded wire as shown in FIG. 13 is used.

In the wire body 46, one core strand 11, nine first strands 42, and nine second strands 44 (a plurality of metal strands, an outer circumferential layer) are twisted together.

In FIG. 13, the second strands 44 are shown to be separated in a circumferential direction. However, this is because cross sections of the first strands 42 and the second strands 44 are schematically represented by a circle.

Since exact cross sections of the first strands 42 and the second strands 44 are ellipses, the strands adjacent to each other in the circumferential direction are actually in contact with each other in the circumferential direction.

The core strand 11 of this modification has the same constitution as the core strand 11 of the above embodiment, and extends along a central axis $O_{46}$ of the wire body 46.

The first strands 42 are metal strands that are twisted at an outer circumferential portion of the core strand 11. However, a strand diameter of each of the first strands 42 is smaller than that of the core strand 11.

The core strand 11 and the nine first strands 42 constitute a 1×10 strand 43. A twisting direction of the first strands 42 is not limited.

The second strands 44 are metal strands that extend along the central axis $O_{44}$, and have a larger strand diameter than the first strands 42 twisted to be adjacent to each other at an outer circumferential portion of the strand 43 in a circumferential direction. A twisting direction of the second strands 44 is not limited.

The nine second strands 44 constitute the outer circumferential layer of the wire body 46.

For example, as a specific example of the wire body 46, SUS403 having diameters of 0.15 mm, 0.1 mm, and 0.15 mm may be used as the core strand 11, the first strands 42, and the second strands 44. In this case, a wire diameter of the wire body 46 is 0.6 mm.

In the same way as the above embodiment, in each of the second strands 44, solid lubrication films 15 similar to the above embodiment are formed on outer circumference-side surfaces 44a (outside exposure surfaces), each of which is an area of a major arc between contact portions of the neighboring second strands 44. However, in the case where a minimum virtual circle in which the second strands 44 are included is assumed to be a circle $C_{46}$, the solid lubrication films 15 of this modification are distributed inside and outside the circle $C_{46}$ in a cross section perpendicular to the central axis $O_{46}$ (hereinafter referred to as a perpendicular cross section).

In the perpendicular cross section of this modification, a part of an outer edge of the solid lubrication film 15 is inside the circle $C_{46}$. Furthermore, when the size (a cross-sectional area) of a portion outside the circle $C_{46}$ in the perpendicular cross section is $A_{15}$, and the size (a cross-sectional area) of a portion inside the circle $C_{46}$ is $B_{15}$, the solid lubrication film 15 of this modification satisfies $A_{15}/B_{15}>0.7$.

Therefore, in the manipulation wire 40, any of the contact portions of the second strands 44 adjacent to each other in the circumferential direction is not covered by the solid lubrication film 15.

This manipulation wire 40 is manufactured in the same way as the above embodiment after the wire body 46 is manufactured.

In the same way as the manipulation wire 10 of the above embodiment, the manipulation wire 40 has slidability for the member of the contact target, and can smoothly transmit rotation about an axis even in a bent state.

Likewise, even if the manipulation wire 40 is bent, the endoscopic device 1C having the manipulation wire 40 can be smoothly operated by forward/backward movement and rotation of the manipulation wire 40.

In the description of the above embodiment and each modification, the case where the solid lubrication film has a constitution in which the solid particles that are lubricativity imparting substance of a fluorine resin are mixed has been described by way of example. However, the solid lubrication film is not limited to this constitution as long as necessary slidability is obtained. For example, the solid lubrication film may be configured such that a resin material having a low friction coefficient extends in a layered shape without containing the solid particles.

In the description of the above embodiment and each modification, the case of the treatment tool in which the medical device is a rotary clip device has been described by way of example. However, if the wire for the medical device of the present invention is used, the medical device of the present invention is not limited to this endoscopic device. For example, the medical device of the present invention may be a treatment tool such as gripping forceps, a guide wire or the like, an endoscope, a surgical treatment tool, or the like.

In the description of the above embodiment and each modification, the case where the solid lubrication film is formed on the outside exposed surface of the outer circumferential layer of the wire body has been described by way of example. However, the solid lubrication film may also be formed on surfaces of the metal strands of the outer circumferential layer except the outside exposed surface, for example, the inner circumference-side surfaces 14b of the above embodiment. However, the cross-sectional area of the solid lubrication film on the inner circumference-side surfaces 14b in the perpendicular cross section is limited to a range satisfying A/B>0.7 because it is included in B.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

For example, the solid lubrication film in the wire for a medical device of the present invention may be configured to include two or more of the aspects of the above embodiment, the first modification, and the second modification on the outside exposed surface of the plurality of metal strands constituting the outer circumferential layer.

What is claimed is:
1. A wire for a medical device comprising:
  a wire body having an outer circumferential layer formed of a plurality of metal strands twisted with each other; and
  a cured solid lubrication film, which is cured to be solid, and which is formed at least on outside exposed surfaces of the plurality of metal strands,
  wherein in at least a part of the wire body in a longitudinal direction, when a virtual circle as a smallest circle enclosing the outer circumferential layer is assumed in a cross section perpendicular to a central axis of the wire body;
  a part of an outer edge of the cured solid lubrication film is inside the virtual circle in the cross section, and
  a cross-sectional area of the cured solid lubrication film in the cross section satisfies A/B>0.7 where A is a size of a portion outside the virtual circle and B is a size of a portion inside the virtual circle.
2. The wire according to claim 1, wherein a thickness of the cured solid lubrication film is 0.01 mm or less at a portion where the outer edge of the cured solid lubrication film is inside the virtual circle in the cross section.

3. The wire according to claim 1, wherein the cured solid lubrication film contains solid particles of a fluorine resin.

4. The wire according to claim 3, wherein the fluorine resin is polytetrafluoroethylene (PTFE).

5. The wire according to claim 1, wherein the wire body includes a plurality of interior metal strands at an interior of the outer circumferential layer formed of the plurality of metal strands twisted with each other, and wherein the cured solid lubrication film is not provided the interior metal strands.

6. The wire according to claim 1, wherein the wire body includes:

a core strand;

a plurality of interior metal strands twisted with each other at an outer circumference of the core strand; and the plurality of metal strands of the outer circumferential layer, which is exterior to the plurality of interior metal strands.

7. The wire according to claim 6, wherein the cured solid lubrication film is provided only on the plurality of metal strands of the outer circumferential layer.

8. The wire according to claim 1, wherein the cured solid lubrication film is provided discontinuously in a circumferential direction of the outer circumferential layer in the cross section.

9. The wire according to claim 1, wherein, in the cross section, the cured solid lubrication film is not provided at contact points between adjacent wire strands among the plurality of metal strands of the outer circumferential layer, such that the cured solid lubrication film is provided discontinuously in a circumferential direction of the outer circumferential layer in the cross section.

10. The wire according to claim 1, wherein the cured solid lubrication film comprises:

film main bodies provided discontinuously in a circumferential direction of the outer circumferential layer in the cross section, on portions of the plurality of metal strands of the outer circumferential layer other than contact points between adjacent wire strands among the plurality of metal strands of the outer circumferential layer; and interstrand films provided on contact points between adjacent wire strands among the plurality of metal strands of the outer circumferential layer.

11. The wire according to claim 10, wherein the film main bodies and the interstrand films are separated from each other along the circumferential direction of the outer circumferential layer in the cross section.

12. The wire according to claim 1, wherein the cured solid lubrication film is provided continuously on all outer circumferential-side surfaces of the plurality of metal strands of the outer circumferential layer.

13. The wire according to claim 12, wherein, in the cross section, the cured solid lubrication film is thinner at portions thereof inside the virtual circle than at portions thereof outside the virtual circle.

14. A medical device comprising:

a sheath;

the wire according to claim 1, wherein the wire extends through the sheath; and a manipulator coupled to a proximal end of the wire, the manipulator being operable to advance and retract the wire.

15. A medical device comprising:

a sheath;

a tube coupled to a distal end of the sheath;

the wire according to claim 1, wherein the wire extends through the sheath;

a clip coupled to a distal end of the wire; and a manipulator coupled to a proximal end of the wire, wherein the manipulator is operable to advance and retract the wire, to advance and retract the clip with respect to the tube, which causes the clip to open and close.

* * * * *